United States Patent
Richter et al.

[11] 3,996,352
[45] * Dec. 7, 1976

[54] ACARICIDAL COMPOSITIONS OF PHOSPHORAMIDATE ESTERS

[75] Inventors: Sidney B. Richter, Chicago; Leonard J. Stach, Riverside, both of Ill.

[73] Assignee: Velsicol Chemical Corporation, Chicago, Ill.

[ * ] Notice: The portion of the term of this patent subsequent to June 11, 1991, has been disclaimed.

[22] Filed: May 12, 1975

[21] Appl. No.: 576,765

Related U.S. Application Data

[60] Continuation of Ser. No. 433,185, Jan. 14, 1974, abandoned, which is a division of Ser. No. 115,079, Feb. 12, 1971, Pat. No. 3,816,620, which is a division of Ser. No. 778,768, Nov. 25, 1968, Pat. No. 3,632,814.

[52] U.S. Cl. .................. 424/200; 260/294.8 K; 260/295 AM; 260/295.5 A
[51] Int. Cl.² ......................... A01N 9/36
[58] Field of Search ........... 260/294.8 K, 295 AM, 260/295.5 A; 424/263

[56] References Cited
UNITED STATES PATENTS

| | | | |
|---|---|---|---|
| 3,632,814 | 1/1972 | Richter et al. | 260/294.8 K |
| 3,748,335 | 7/1973 | Richter et al. | 260/294.8 K |

Primary Examiner—Alan L. Rotman
Attorney, Agent, or Firm—Robert J. Schwarz; Dietmar H. Olesch

[57] ABSTRACT

This invention discloses new compounds of the formula

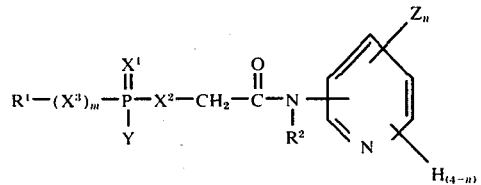

wherein $R^1$ is selected from the group consisting of alkyl, alkenyl and

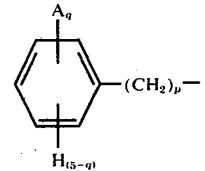

wherein A is selected from the group consisting of alkyl, alkenyl, alkoxy, alkylthio, halogen, nitro, dialkylamino, alkylsulfoxide and alkylsulfone, q is an integer from 0 to 5, and p is an integer from 0 to 3; $X^1$, $X^2$ and $X^3$ are independently selected from the group consisting of oxygen and sulfur; m is an integer from 0 to 1; Y is selected from the group consisting of alkyl, alkenyl, alkoxy, alkylthio, amino, alkylamino, dialkylamino and

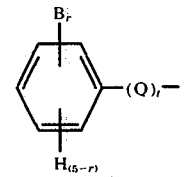

wherein B is selected from the group consisting of alkyl, alkenyl, alkoxy, alkylthio, halogen, nitro, dialkylamino, alkylsulfoxide and alkylsulfone, r is an integer from 0 to 5, Q is selected from the group consisting of oxygen, sulfur, alkylene, alkyleneoxy and alkylenethio, and t is an integer from 0 to 1; $R^2$ is alkyl; Z is selected from the group consisting of alkyl, alkenyl, alkoxy, alkylthio, halogen and nitro; and n is an integer from 0 to 4. The above described compounds are useful as pesticides, particularly as insecticides and acaricides.

2 Claims, No Drawings

ACARICIDAL COMPOSITIONS OF PHOSPHORAMIDATE ESTERS

This is a continuation of copending application Ser. No. 433,185, filed Jan. 14, 1974 now abandoned; which is a division of Ser. No. 115,079, filed Feb. 12, 1971, now issued into U.S. Pat. No. 3,816,620; which is a division of Ser. No. 778,768, filed Nov. 25, 1968, now issued into U.S. Pat. No. 3,632,814.

This invention relates to new chemical compositions and more particularly relates to new compounds of the formula

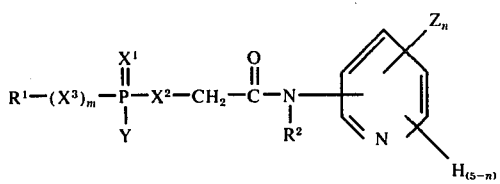

wherein $R^1$ is selected from the group consisting of alkyl, alkenyl and

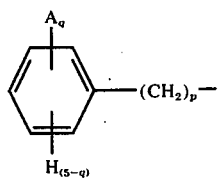

wherein A is selected from the group consisting of alkyl, alkenyl, alkoxy, alkylthio, halogen, nitro, dialkylamino, alkylsulfoxide and alkylsulfone, q is an integer from 0 to 5, and p is an integer from 0 to 3; $X^1$, $X^2$ and $X^3$ are independently selected from the group consisting of oxygen and sulfur; $m$ is an integer from 0 to 1; Y is selected from the group consisting of alkyl, alkenyl, alkoxy, alkylthio, amino, alkylamino, dialkylamino and

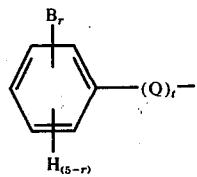

wherein B is selected from the group consisting of alkyl, alkenyl, alkoxy, alkylthio, halogen, nitro, dialkylamino, alkylsulfoxide and alkylsulfone, r is an integer from 0 to 5, Q is selected from the group consisting of oxygen, sulfur, alkylene, alkyleneoxy and alkylenethio, and t is an integer from 0 to 1; $R^2$ is alkyl; Z is selected from the group consisting of alkyl, alkenyl, alkoxy, alkylthio, halogen and nitro; and n is an integer from 0 to 4.

In a preferred embodiment of this invention $R^1$ is selected from the group consisting of lower alkyl, lower alkenyl and

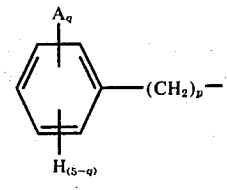

wherein A is selected from the group consisting of lower alkyl, lower alkenyl, lower alkoxy, lower alkylthio, chlorine, bromine, nitro and di(lower alkyl)amino, q is an integer from 0 to 3, and $p$ is an integer from 0 to 2; $X^1$, $X^2$ and $X^3$ are independently selected from the group consisting of oxygen and sulfur; m is an integer from 0 to 1; Y is selected from the group consisting of lower alkyl, lower alkenyl, lower alkoxy, lower alkylthio, amino, lower alkylamino, di(lower alkyl)amino and

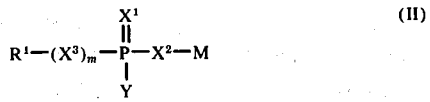

wherein B is selected from the group consisting of lower alkyl, lower alkenyl, lower alkoxy, lower alkylthio, chlorine, bromine, nitro and di(lower alkyl)amino, r is an integer from 0 to 3, Q is selected from the group consisting of oxygen, sulfur, alkylene of up to 4 carbon atoms, metholoxy, ethyloxy, methylthio and ethylthio, and t is an integer from 0 to 1; $R^2$ is lower alkyl; Z is selected from the group consisting of lower alkyl, lower alkenyl, lower alkoxy, lower alkylthio, chlorine, bromine and nitro; and n is an integer from 0 to 3.

The new compounds of the present invention are unexpectedly useful as pesticides particularly as insecticides and acaricides.

The compounds of the present invention can be readily prepared by reacting an alkali metal salt of a phosphorus acid of the formula $$R^1-(X^3)_m-\overset{\overset{X^1}{\|}}{\underset{Y}{P}}-X^2-M \qquad (II)$$

wherein M is an alkali metal such as potassium; and $X^1$, $X^2$, $X^3$, Y, $R^1$ and m are heretofore described, with an N-pyridyl-α-chloroacetamide of the formula

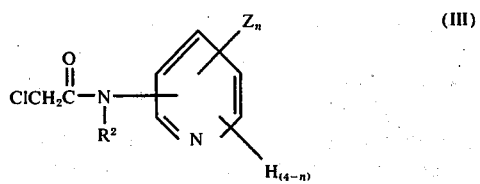

wherein $R^2$, Z and $n$ are as heretofore described. This reaction can be effected by heating the above reactants in an inert organic reaction medium at the reflux temperature of the reaction mixture for a period of from about 1 to about 48 hours. The desired product can then be recovered by first filtering the reaction mixture to remove the alkali metal chloride which is formed and thereafter stripping the mixture of the solvent used as the reaction medium to yield the product as a residue. This residue can be used as such to prepare valuable insecticidal and acaricidal compositions or it can be further purified, if desired, by washing, extraction, recrystallizing, chromatography or other techniques well known in the art.

The phosphorus acid salts of Formula II, when not readily available, can be prepared from their corresponding acids by the methods described by Malatesta and Pizzotti, Chimica e Industria (Milan) 27, 6–10 (1945), and Melnikov and Grapov, Zhur. Vsesoyuz Khim. Obshchestva in D. I. Mendeleeva, 6, No. 1, 119–120 (1961).

The N-pyridyl-α-chloroacetamides of Formula III can be prepared by reacting chloroacetyl chloride with an aminopyridine or alkylaminopyridine having the desired substituents on the pyridine ring. This reaction can be effected by adding chloroacetyl chloride or a solution of chloroacetyl chloride in a suitable solvent such as ether, for example, to a solution of the aminopyridine or alkylaminopyridine in an inert organic solvent at a temperature below about 50° C and preferably at a temperature of from about −20° to about 30° C in the presence of an acid acceptor such as a tertiary amine or alkali metal hydroxide or carbonate. The desired product can then be recovered as the residue upon evaporation of the solvents used, or by filtration of the reaction mixture if the product forms as a precipitate. The product can then be used as such or can be further purified by conventional techniques for use in preparing the compounds of the present invention.

The manner in which the compounds of this invention can be prepared readily is more specifically illustrated by the following examples.

EXAMPLE 1

Preparation of
N-(6-Methoxy-3-pyridyl)-α-chloroacetamide

A solution of 3-amino-6-methoxypyridine (25.0 grams) in absolute ether (160 ml) was charged into a glass reaction flask equipped with a mechanical stirrer, dropping funnel and thermometer. The solution was cooled to a temperature of about 0° C and pyridine (18.1 ml) was added thereto. A solution of chloroacetyl chloride (17.0 ml) in ether (40 ml) was then slowly added to the flask with stirring over a period of about 15 minutes resulting in the formation of a precipitate. The temperature of the reaction mixture was kept between about 0° to 5° C during the addition of the chloroacetyl chloride. After completion of the addition stirring was continued for a period of about 30 minutes. The solid precipitate which had formed was then recovered by filtration and was washed with aqueous sodium bicarbonate and then with water. The washed product was then dried to yield the desired product N-(6-methoxy-3-pyridyl)-α-chloroacetamide as a white solid having a melting point of 117° to 118° C.

EXAMPLE 2

Preparation of
S-[2-(6-Methoxy-3-pyridylamino)-2-ketoethyl]
O-Ethyl N-Isopropylthiolophosphoramidate N-(6-Methoxy-3-pyridyl)-α-chloroacetamide (10.0 grams), acetone (175 ml) and potassium O-ethyl N-isopropylthiolophosphoramidate (16.5 grams) were charged into a glass reaction flask equipped with a mechanical stirrer, thermometer and reflux condenser. The reaction mixture was heated at reflux with stirring for a period of about 24 hours. After this time the reaction mixture was stripped of acetone on a steam bath leaving a red colored residue. The residue was dissolved in ether (130 ml) and was washed with water. The washed solution was dried over sodium sulfate, was filtered and evaporated to yield a red oil. The oil was placed into a vacuum desiccator and dried under vacuum (2.0 mm) at room temperature for a period of about 4 hours. The oil was then allowed to stand for several days upon which it solidified to yield the desired product S-[2-(6-methoxy-3-pyridylamino)-2-ketoethyl] O-ethyl N-isopropylthiolophosphoramidate as a crystalline solid having a melting point of 85° to 86° C.

EXAMPLE 3

Preparation of
S-[2-(6-Methoxy-3-pyridylamino)-2-ketoethyl]
O-Ethyl N-t-Butylthiolophosphoramidate N-(6-Methoxy-3-pyridyl)-α-chloroacetamide (4.5 grams), acetone (150 ml) and potassium O-ethyl N-t-butylthiolophosphoramidate (6.78 grams) were charged into a glass reaction vessel equipped with stirrer, thermometer and reflux condenser. The reaction mixture was heated at reflux, with stirring, for a period of about 24 hours. After this time the reaction mixture was cooled to room temperature, was filtered and stripped of acetone to yield a red viscous residue. The residue was dissolved in chloroform. The chloroform solution was washed with water and dried over magnesium sulfate. The dried solution was filtered and evaporated to yield the desired product S-[2-(6-methoxy-3-pyridylamino)-2-Ketoethyl] O-ethyl N-t-butylthiolophosphoramidate as a red viscous oil.

EXAMPLE 4

Preparation of S-[2-(6-Methoxy-3-pyridylamine 2-ketoethyl] O,O-Dimethyl Thiolothionophosphate N-(6-Methoxy-3-pyridyl)-α-chloroacetamide (8.0 grams), potassium O,O-dimethyl thiolothionophosphate (9.41 grams) and acetone (100 ml) were charged into a glass reaction flask equipped with stirrer, thermometer and reflux condenser. The reaction mixture was heated at reflux with stirring for a period of about 16 hours. After this time the reaction mixture was cooled, filtered and stripped of acetone to yield a residue. The residue was extracted with chloroform and the chloroform solution washed with water and dried over sodium sulfate. The dried solution was filtered and evaporated on a steam bath under vacuum to yield the desired product S-[2-(6-methoxy-3-pyridylamino)-2-ketoethyl] O,O-dimethyl thiolothionophosphate as a red oil.

EXAMPLE 5

Preparation of N-(4-Methyl-2-pyridyl)-α-chloroacetamide

A solution of 2-amino-4-methylpyridine (10.8 grams) in ether (150 ml), and triethylamine (10 grams) are placed in a reaction flask equipped with stirrer, thermometer and addition funnel. The reaction mixture is cooled to a temperature of about 0° C and chloroacetyl chloride (11.3 grams) dissolved in ether (30 ml) is slowly added thereto resulting in the formation of a precipitate. Stirring is continued for a period of about 1 hour. After this time the reaction mixture is filtered to recover the precipitate that has formed. The precipitate is washed with aqueous potassium carbonate and with water. The washed precipitate is then dried to yield the desired product N-(4-methyl-2-pyridyl)-α-chloroacetamide.

EXAMPLE 6

Preparation of O-[2-(4-Methyl-2-pyridylamino)-2-ketoethyl] O-(3,4-Dichlorophenyl) Methylphosphonate N-(4-Methyl-2-pyridyl)-α-chloroacetamide (18.5 grams), potassium O-(3,4-dichlorophenyl) methylphosphonate (29.5 grams) and acetone (150 ml) are charged into a glass reaction vessel equipped with a mechanical stirrer, thermometer and reflux condenser. The reaction mixture is stirred and heated at reflux for a period of about 18 hours. After this time the reaction mixture is cooled, filtered and stripped of acetone on a steam bath to yield a residue. The residue is extracted with chloroform and the chloroform solution is washed with water. The washed solution is dried over magnesium sulfate, is filtered and evaporated to yield the desired product O-[2-(4-methyl-2-pyridylamino)-2-ketoethyl] O-(3,4-dichlorophenyl) methylphosphonate as the residue.

EXAMPLE 7

Preparation of N-(2-Chloro-6-ethoxy-3-pyridyl)-α-chloroacetamide

A solution of 2-chloro-3-amino-6-ethoxypyridine (17 grams) in ether (200 ml), and triethylamine (10 grams) are placed in a glass reaction flask equipped with stirrer, thermometer and addition funnel. The mixture is cooled to about 0° to 10° C and a solution of chloroacetyl chloride (11.3 grams) in ether (40 ml) is slowly added thereto over a period of about 30 minutes resulting in the formation of a precipitate. The precipitate is recovered by filtration and is washed first with aqueous sodium bicarbonate and then with water. The washed product is then dried to yield the desired product N-(2-chloro-6-ethoxy-3-pyridyl)-α-chloroacetamide.

EXAMPLE 8

Preparation of O-[2-(2-Chloro-6-ethoxy-3-pyridylamino)-2-ketoethyl] S,S-Diisopropyl Dithiolophosphate N-(2-Chloro-6-ethoxy-3-pyridyl)-α-chloroacetamide (25.1 grams), potassium S,S-diisopropyl dithiolophosphate (25.2 grams) and acetone (250 ml) are charged into a glass reaction flask equipped with stirrer, thermometer and reflux condenser. The reaction mixture is then refluxed for a period of about 36 hours. After this time the mixture is stripped of solvent and the resulting residue is dissolved in chloroform. The chloroform solution is washed with water and is dried over magnesium sulfate. The dried solution is filtered and evaporated to yield the desired product O-[2-(2-chloro-6-ethoxy-3-pyridylamino)-2-ketoethyl] S,S-diisopropyl dithiolophosphate.

EXAMPLE 9

Preparation of N-(3-Methoxy-5-bromo-2-pyridyl)-α-chloroacetamide

A solution of 2-amino-3-methoxy-5-bromopyridine (20.3 grams) in absolute ether (200 ml) is charged into a glass reaction vessel equipped with mechanical stirrer and addition funnel. The solution is cooled to a temperature of about 5° C and pyridine (20 ml) is added thereto. A solution of chloroacetyl chloride (11.3 grams) in ether (50 ml) is then slowly added, with stirring, to the flask over a period of about 30 minutes resulting in the formation of a precipitate. The temperature of the reaction mixture is kept below about 10° C during the addition of the chloroacetyl chloride and stirring is continued thereafter for a period of about 1 hour to ensure the completion of the reaction. The precipitate which has formed is then recovered by filtration and is washed first with aqueous potassium carbonate and then with water. The washed product is then dried in a vacuum desiccator to yield the desired product N-(3-methoxy-5-bromo-2-pyridyl)-α-chloroacetamide.

EXAMPLE 10

Preparation of O-[2-(3Methoxy-5-bromo-2-pyridylamino)-2-ketoethyl] N,N-Dimethyl Methylphosphonamidate N-(3-Methoxy-5-bromo-2-pyridyl)-α-chloroacetamide (28.0 grams), potassium N,N-dimethyl methylphosphonamidate (16.1 grams) and acetone (200 ml) are charged into a glass reaction 2-pyridyl)-αequipped with a mechanical stirrer, thermometer and reflux condenser. The reaction mixture is heated at reflux for a period of about 18 hours. After this time the mixture is stripped of acetone on the steam bath and the resulting residue is dissolved in ether (200 ml) and is washed with water. The washed solution is dried over magnesium sulfate, is filtered and evaporated to yield the desired product O-[2-(3-methoxy-5-bromo-2-pyridylamino)-2-ketoethyl] N,N-dimethyl methylphosphonamidate.

EXAMPLE 11

Preparation of N-(4-Nitro-6-ethoxy-2-pyridyl)-α-chloroacetamide

A solution of 2-amino-4-nitro-6-ethoxypyridine (29.4 grams) in absolute ether (150 ml), and pyridine (25 grams) are charged into a glass reaction vessel equipped with stirrer, thermometer and addition funnel. The mixture is cooled to a temperature of about 0° C and chloroacetyl chloride (11.3 grams) dissolved in ether (50 ml) is then slowly added thereto with stirring over a period of about 20 minutes. Stirring and cooling are continued for an additional period of about 30 minutes. The resulting precipitate is then recovered from the reaction medium by filtration, is washed first with aqueous sodium carbonate and then with water, and is dried to yield the desired product N-(4-nitro-6-ethoxy-2-pyridyl)-α-chloroacetamide.

EXAMPLE 12

Preparation of
S-[2-(4-Nitro-6-ethoxy-2-pyridylamino-2-ketoethyl]
Diisopropylthiolophosphinate N-(4Nitro-6-ethoxy-2-pyridyl)-α-chloroacetamide (37.1 grams) and potassium diisopropylthiolophosphinate (12.2 grams) and acetone (250 ml) are charged into a glass reaction vessel equipped with mechanical stirrer, thermometer and reflux condenser. The reaction mixture is heated at reflux for a period of about 36 hours. After this time the reaction mixture is stripped of solvent on a steam bath and the resulting residue is dissolved in ether (150 ml) and is washed with water. The washed solution is then dried over anhydrous magnesium sulfate, is filtered and evaporated to yield the desired product S-[2-(4-nitro-6-ethoxy-2-pyridylamino)-2-ketoethyl] diisopropylthiolophosphinate.

EXAMPLE 13

Preparation of
N-(2,6-Dimethyl-3-pyridyl)-α-chloroacetamide

A solution of 2,6-dimethyl-3-aminopyridine (24.9 grams) in ether (200 ml), and pyridine (21 grams) are charged into a glass reaction vessel equipped with mechanical stirrer, thermometer and addition funnel. The reaction mixture is cooled to a temperature below about 10° C and chloroacetyl chloride (11.3 grams) is slowly added over a period of about 15 minutes. Stirring and cooling is continued for an additional period of about 1 hour to ensure the completion of the reaction. The resulting precipitate is then recovered by filtration, is washed with aqueous potassium carbonate and with water, and is dried to yield the desired product N-(2,6-dimethyl-3-pyridyl)-α-chloroacetamide.

EXAMPLE 14

Preparation of O-[2-(2,6-Dimethyl-32-ketoethyl]
O-Methyl O-(4-Chlorophenyl) Phosphate N-(2,6-Dimethyl-3-pyridyl)-α-chloroacetamide (32.2 grams), potassium O-methyl O-(4-chlorophenyl) phosphate (26 grams) and acetone (200 ml) are charged into a glass reaction vessel equipped with a mechanical stirrer, thermometer and reflux condenser. The reaction mixture is heated at reflux for a period of about 24 hours. After this time the mixture is stripped of solvent on a steam bath and the resulting residue is dissolved in ether. The ether solution is washed with water and is dried over magnesium sulfate. The dried solution is then evaporated under vacuum to yield the desired product O-[2-(2,6-dimethyl-3-pyridylamino)-2-ketoethyl] O-methyl O-(4-chlorophenyl) phosphate.

Additional compounds within the scope of the present invention can be prepared in a manner similar to that detailed in the foregoing examples. In the following examples are given the essential ingredients required to prepare the indicated named compounds by the procedures heretofore described.

EXAMPLE 15

2-Amino-3,5-diiodopyridine + chloroacetyl chloride + potassium diphenylthionophosphinate = O-[2-(3,5-diiodo-2-pyridylamino)-2-ketoethyl] diphenylthionophosphinate.

EXAMPLE 16

4-Amino-2,6-dichloropyridine + chloroacetyl chloride + potassium (2-chloro-4-nitrophenyl) (3,4-dibromophenyl)phosphinate = O-[2-(2,6-dichloro-4-pyridylamino)2-ketoethyl] (2-chloro-4-nitrophenyl) (3,4-dibromophenyl)phosphinate.

EXAMPLE 17

2-Amino-3-ethoxy-6-nitropyridine + chloroacetyl chloride + potassium ethyl(2-methyl-4-nitrophenyl)-phosphinate = O-[2-(3-ethoxy-6-nitro-2-pyridylamino)-2-ketoethyl] ethyl-(2-methyl-4-nitrophenyl)phosphinate.

EXAMPLE 18

3-Amino-6butoxypyridine + chloroacetyl chloride + potassium (2-methoxy-4-chlorophenyl) (4-isopropylphenyl)-phosphinate = O-[2-(6-butoxy-3-pyridylamino)-2-ketoethyl] (2-methoxy4-chlorophenyl) (4-isopropylphenyl)phosphinate

EXAMPLE 19

3-Amino-4-n-butyl-6-methoxypyridine + chloroacetyl chloride + potassium O-(3-methylthiophenyl) t-butylphosphonate = O-[2-(4-n-butyl-3pyridylamino)-2-ketoethyl] O-(3-methylthiophenyl) t-butylphosphonate.

EXAMPLE 20

4-Amino-3-bromopyridine + chloroacetyl chloride + potassium S-(3-allyl-5-ethylphenyl) 4-dimethylaminophenyl-dithiolophosphonate = S-[2-(3-bromo-4-pyridylamino)-2-keto-ethyl] S-(3-allyl-5-ethylphenyl) 4-dimethylaminophenyldithiolophosphonate.

EXAMPLE 21

3-Amino-5-allylpyridine + chloroacetyl chloride + potassium O-(3-methylsulfonylphenyl) O-(4-methylthiophenyl) phosphate = O-[2-(5-allyl-3-pyridylamino)-2-ketoethyl] O-(3-methylsulfonylphenyl) O-(4-methylthiophenyl) phosphate.

EXAMPLE 22

3-Amino-5-bromo-2,4-dichloropyridine + chloroacetyl chloride + potassium S-(3-dimethylaminophenyl) O-(2,4-dichlorobenzyl) thiolophosphate = O-[2-(5bromo-2,4-dichloro-3-pyridylamino)-2-ketoethyl] S-(3-dimethylaminophenyl) O-(2,4-dichlorobenzyl) thiolophosphate.

EXAMPLE 23

2-Amino-5-chloro-3-nitropyridine + chloroacetyl chloride + potassium O-pentenyl N,N-diethylphosphoramidate = O-[2-(5-chloro-3-nitro-2-pyridylamino)-2-ketoethyl] O-pentenyl N,N-diethylphosphoramidate.

EXAMPLE 24

4-Amino-2,5-dinitropyridine + chloroacetyl chloride + potassium S-(2-n-propoxy-4-bromophenyl) N-methyl-N-sec-butylthiolothionophosphoramidate = O-[2-(2,5-dinitro-4-pyridylamino)-2-ketoethyl] S-(2-n-propoxy-4-bromophenyl) N-methyl-N-sec-butylthiolothionophosphoramidate.

EXAMPLE 25

2-Amino-3,5-dibromo-4-ethylpyridine + chloroacetyl chloride + potassium S-isopropyl S-(4-n-pentylsulfinylphenyl) tetrathiophosphate = S-[2-(3,5-dibromo-4-ethyl-2-pyridylamino)-2-ketoethyl] S-isopropyl S-(4-n-pentylsulfinylphenyl tetrathiophosphate.

Additional compounds within the scope of the present invention that can be prepared by the methods detailed in the foregoing examples but which are not intended to limit this invention thereto are:

O-[2-(6-methylthio-3-pyridylamino)-2-ketoethyl] S-t-butylallylthiophosphonate

S-[2-(4-chloro-5-allyl-3-pyridylamino)-2-ketoethyl] O-(2,4-dichloro-6-pentenylphenyl) hexylthiolophosphonate S-[2-(6-isopropyl-4-ethoxy-2-pyridylamino)-2-ketoethyl] S-(2,6-diethoxy-4-iodophenyl) 4-di-n-propylaminophenyldithiolophosphonate O-[2-(5-allyl-2-pyridylamino)2-ketoethyl] O-(3-diethylsulfinylphenyl) 3-n-butoxy-5-allylphenethylthionophosphonate O-[2-(2-n-hexyl-5-chloro-3-pyridylamino-2-ketoethyl] S-(2-n-butylthio-4-isopropylsulfonylphenyl) n-pentylthiolothionophosphonate S-[2-(5-n-decyl-3-pyridylamino)-2-ketoethyl] O-(3-n-octyloxy-5-n-decylphenyl) N,N-di-n-pentylaminothiolophosphoramidate O-[2-(6-n-decyloxy-2-pyridylamino)-2-ketoethyl] O-n-heptyl O-(4-di-n-hexylamino-phenyl phosphate O-[2-(4-t-butylthio-2-pyridylamino)-2-ketoethyl] (2-n-octyl-4-nitrophenyl) (2,4-dichloro-6-ethylthiobenzyl)thionophosphinate O-[2-(6-n-decylthio-4-iodo-3-pyridylamino)-2-ketoethyl] O-[3-(2,4-dichlorophenyl)propyl] O-(4-di-n-decylaminobenzyl)thionophosphate S-[2-(6-methoxy-3-pyridylamino)-2-ketoethyl] O,O-di-n-decyl thiolophosphate S-[2-(4-chloro-6-methoxy-32-ketoethyl] S,S-di-t-butyl tetrathiophosphate S-{2-[N-(6-methoxy-3-pyridyl)-N- methylamino]-2-ketoethyl} O-ethyl N-isopropylthiolophosphoramidate O-{2-[N-(6-methoxy-3,4-dichloro-2-pyridyl)-n-isopropylamino]-2-ketoethyl} O,O-dimethylphosphate O-{2-[N-(3-ethoxy-6-nitro-2-pyridyl)-N-n-decylamino]-2-ketoethyl, O-(4-chlorophenyl) isopropylphosphonate For practical use as insecticides or acaricides, the compounds of this invention are generally incorporated into insecticidal or acaricidal compositions which comprise an inert carrier and an insecticidally or acaricidally toxic amount of such a compound. Such insecticidal or acaricidal compositions, which can also be called formulations, enable the active compound to be applied conveniently to the site of the insect of acarid infestation in any desired quantity. These compositions can be solids such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculities, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of insecticides or acaricides can be dispersed under superatmospheric pressure as aerosols. However, preferred liquid insecticidal or acaricidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the insect or acarid infestation. The emulsifiers most commonly used in these concentrates are nonionic or mixtures of nonionic with anionic surface-active agents.

A typical insecticidal or acaricidal composition according to this invention is illustrated by the following example, in which the quantities are in parts by weight.

EXAMPLE 26

Preparation of a Dust

| Product of Example 2 | 10 |
| --- | --- |
| Powdered Talc | 90 |

The above ingredients are mixed in a mechanical grinder-blender and are ground until a homogeneous, free-flowing dust of the desired particle size is obtained. This dust is suitable for direct application to the site of the insect or acarid infestation.

The compounds of this invention can be applied as insecticides or acaricides in any manner recognized by the art. One method for destroying insects or acarids comprises applying to the locus of the insect or acarid infestation an insecticidal or acaricidal composition comprising an inert carrier and, as an essential active ingredient, in a quantity which is toxic to said insects or acarids, a compound of the present invention. The concentration of the new compounds of this invention in the insecticidal or acaricidal compositions will vary greatly with the type of formulation and the purpose for which it is designed, but generally the insecticidal or acaricidal compositions will comprise from about 0.05 to about 95 percent by weight of the active compounds of this invention. In a preferred embodiment of this invention, the insecticidal or acaricidal compositions will comprise from about 5 to 75 percent by weight of the active compound. The compositions can also comprise such additional substances as other pesticides, stabilizers, spreaders, deactivators, adhesives, stickers, fertilizers, activators, synergists, and the like.

The compounds of the present invention are also useful when combined with other insecticides or acaricides in the compositions heretofore described. These other insecticides or acaricides can comprise from about 5% to about 95% of the active ingredients in the compositions. Use of the combinations of these other insecticides or acaricides with the compounds of the present invention provide insecticidal and/or acaricidal compositions which are more effective in controlling insects or acarids and often provide results unattainable with separate compositions of the individual compounds. The other insecticides or acaricides with which the compounds of this invention can be used in the insecticidal or acaricidal compositions to control insects or acarids include halogenated compounds such as DDT, methoxychlor, TDE, lindane, chlordane, isobenzan, aldrin, dieldrin, heptachlor, endrin, mirex, endosulfon, dicofol, and the like; organic phosphorus compounds such as TEPP, schradan, ethion, parathion, methyl parathion, EPN, demeton, carbophenothion, phorate, zinophos, diazinon, malathion, mevinphos, dimethoate, DBD, ronnel, oxydemeton-methyl, dicapthon, chlorothion, phosphamidon, naled, fenthion, trichlorofon, DDVP, and the like; organic nitrogen compounds such as dinitro-o-cresol. dinitrocyclohexylphenol, DNB, DNp, binapacril, azobenzene, and the like; organic carbamate compounds such as carbaryl, ortho 5353, and the like; organic sulfur compounds such as phenothiazine, phenoxathin, lauryl thiocyanate, [bis(2-thiocyanoethyl)ether], isobornyl thiocyanoacetate, and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene, and the like.

The compounds of the present invention can also be combined with fungicidal and nematocidal chemical compounds to form pesticidal compositions useful for the control of fungi and in some cases soil nematodes as well as insects or acarids. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate, and the like; while examples of nematocidal compounds are chloropicrin, O,O-diethyl O-(2,4-dichlorophenyl)phosphorothioate, tetrachlorothiophene, dazomet, dibromochloropropane, and the like.

The new compounds of this invention can be used in many ways for the control of insects or acarids. Insecticides or acaricides which are to be used as stomach poisons or protective materials can be applied to the surface on which the insects or acarids feed or travel. Insecticides or acaricides which are to be used as contact poisons or eradicants can be applied directly to the body of the insect or acarid, as a residual treatment to the surface on which the insect or acarid may walk or crawl, or as a fumigant treatment of the air which the insect or acarid breathes. In some cases, the compounds applied to the soil or plant surfaces are taken up by the plant, and the insects or acarids are poisoned systemically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beetle and the southern armyworm; the piercing-sucking insects, such as the pea aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms or weevils, such as the codling moth, the alfalfa weevil, the cotton boll weevil, the pink boll worm, the plum curculio, the red banded leaf roller, the melonworm, the cabbage looper and the apple maggot, leaf miners, such as the apple leaf miner, the birch leaf miner and the beet leaf miner, and gall insects, such as the wheat joint worm and the grape phylloxera. Insects which attack below the surface of the ground are classified as subterranean insects and include such destructive pests as the woolly apple aphid, the Japanese beetle, the onion maggot and the corn rootworm.

Mites and ticks are not true insects. Many economically important species of mites and ticks can be controlled by the compounds of the present invention, such as the red spider mite, the two-spotted mite, the strawberry spider mite, the citrus rust mite, the cattle tick, the poultry mite, the citrus red mite and the European red mite. Chemicals useful for the control of mites are often called miticides, while those useful for the control of both mites and ticks are known specifically as acaricides.

The quantity of active compound of this invention to be used for insect or acarid control will depend on a variety of factors, such as the specific insect involved, intensity of the infestation, weather, type of environment, type of formulation, and the like. For example, the application of only one or two ounces of active chemical per acre may be adequate for control of a light infestation of an insect or acarid under conditions unfavorable for its feeding, while a pound or more of active compound per acre may be required for the control of a heavy infestation of insects or acarids under conditions favorable to their development.

The insecticidal utility of the compounds of this invention was demonstrated by experiments carried out for the control of a variety of insects.

In one experiment carried out for the control of the housefly, designated as the housefly topical test, each of fifty flies was contacted with a test compound by applying 1 $\mu$ of test formulation, containing the indicated concentrations of active compound, to the dorsum of its thorax. The flies were then placed in a wire mesh cage where they were supplied with sugar syrup. At the end of a 24 hour period the mortality of the flies was observed and rated in comparison to a control. The results of this experiment are shown in Table I.

TABLE I

| Test Compound | Concentration of Test Compound in ppm | % Mortality |
|---|---|---|
| Product of Example 2 | 3500 | 100 |
| Product of Example 3 | 3500 | 92 |
| Product of Example 4 | 3500 | 94 |

The insecticidal activity of the compounds of this invention was further illustrated in experiments carried out for the control of the pea aphid (*Acyrthosiphon pisum*) by contact. In these experiments ten day old Laxton pea plants contained in small plastic pots were each infested with ten adult pea aphids. The plants and pea aphids were then sprayed with the test compound formulated as an aqueous emulsion of an acetone solution at various concentrations. The infested plants were then placed in a holding chamber maintained at a constant temperature for a period of 48 hours. After this time the mortality of the aphids was determined and rated on a percent basis in comparison to a control. The results of this experiment are shown in Table II.

TABLE II

| Test Compound | Concentration of Test Compound in ppm | % Mortality |
| --- | --- | --- |
| Product of Example 2 | 3500 | 100 |
| " | 1000 | 100 |
| " | 100 | 100 |
| Product of Example 3 | 3500 | 100 |
| " | 1000 | 100 |
| " | 100 | 78 |
| Product of Example 4 | 3500 | 100 |

The systemic activity of the compound of this invention was demonstrated in experiments for the systemic control of pea aphids. In these experiments 5 day old Laxton pea plants which had previously been watered with 30 ml of water containing the test compound at the indicated concentration, were infested with ten newly molted adult pea aphids. The infested plants were then placed in a holding chamber at 65° F for a period of 48 hours where they were supplied with water and light as required. After this time the mortality of the pea aphids was determined and rated on a percent basis in comparison to an untreated control. The results of this experiment are given in Table III.

TABLE III

| Test Compound | Concentration of Test Compound in ppm | % Mortality |
| --- | --- | --- |
| Product of Example 2 | 100 | 100 |
| Product of Example 3 | 100 | 100 |

The acaricidal activity of the compounds of the present invention was demonstrated in experiments carried out for the control of the two-spotted spider mite (*Tetranychus urticae*).

In one experiment wherein the activity of the compounds of the present invention as contact poisons was determined, the test compounds were formulated at the indicated dosages, as aqueous emulsions of acetone solutions and were sprayed onto Henderson bush lima bean plants, each infested with about 100 adult two-spotted spider mites. The treated plants were then placed into a holding room and were supplied with their daily requirement of water and light. After a period of 5 days the mortality of the mites is determined and is rated on a percent basis in comparison to untreated controls. The results of this experiment are shown in Table IV.

TABLE IV

| Test Compound | Concentration of Test Compound in ppm | % Mortality |
| --- | --- | --- |
| Product of Example 2 | 3500 | 100 |
| " | 1000 | 100 |
| " | 100 | 98 |
| Product of Example 3 | 3500 | 96 |
| " | 1000 | 85 |
| " | 100 | 40 |

In another experiment the system activity of the compounds of this invention for the control of the two-spotted spider mite was demonstrated. In this experiment 5 day old Henderson bush lima bean plants were each watered with 30 ml of a formulation containing the test compound at the indicated concentration. After a period of 48 hours the plants were infested with two-spotted spider mites and were placed into a holding room and supplied with water and light as required. After a period of 5 days the mortality of the mites is determined and rated on a percent basis in comparison to untreated controls. The results of this experiment are shown in Table V.

TABLE V

| Test Compound | Concentration of Test Compound in ppm | % Mortality |
| --- | --- | --- |
| Product of Example 2 | 100 | 100 |
| " | 80 | 99 |
| " | 40 | 86 |
| Product of Example 3 | 100 | 98 |
| " | 80 | 83 |

We claim:
1. An acaricidal composition comprising an inert carrier and, as an essential active ingredient, in a quantity toxic to acarids, a compound of the formula

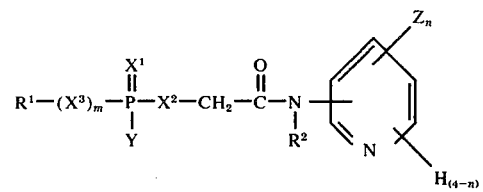

wherein $R^1$ is selected from the group consisting of lower alkyl, lower alkenyl and

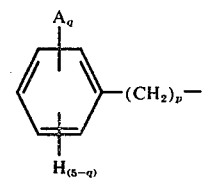

wherein A is selected from the group consisting of lower alkyl, lower alkenyl, lower alkoxy, lower alkylthio, halogen, nitro, diloweralkylamino, lower alkylsulfoxide and lower alkylsulfone, q is an integer from 0 to 5, and p is an integer from 0 to 3; $X^1$, $X^2$ and $X^3$ are independently selected from the group consisting of oxygen and sulfur; m is an integer from 0 to 1; Y is selected from the group consisting of lower alkylamino and diloweralkylamino; $R^2$ is lower alkyl; Z is selected from the group consisting of lower alkyl, lower alkenyl, lower alkoxy, lower alkylthio, halogen and nitro; and n is an integer from 0 to 4.

2. A method of controlling acarids which comprises applying to said acarids an acaricidal composition comprising an inert carrier and, as an essential active ingredient, in a quantity toxic to acarids, a compound of the formula

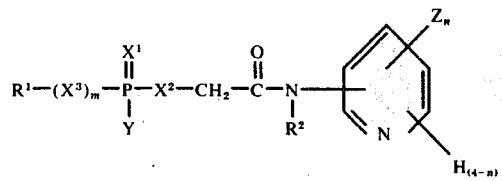

wherein $R^1$ is selected from the group consisting of lower alkyl, lower alkenyl and wherein A is selected from the group consisting of

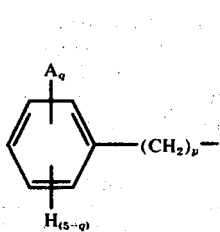

lower alkyl, lower alkenyl, lower alkoxy, lower alkylthio, halogen, nitro, diloweralkylamino, lower alkylsulfoxide and lower alkylsulfone, q is an integer from 0 to 5, and p is an integer from 0 to 3; $X^1$, $X^2$ and $X^3$ are independently selected from the group consisting of oxygen and sulfur; m is an integer from 0 to 1; Y is selected from the group consisting of lower alkylamino and diloweralkylamino; $R^2$ is lower alkyl; Z is selected from the group consisting of lower alkyl, lower alkenyl, lower alkoxy, lower alkylthio, halogen and nitro; and n is an integer from 0 to 4.

* * * * *